(12) United States Patent
Wu et al.

(10) Patent No.: US 7,754,895 B2
(45) Date of Patent: Jul. 13, 2010

(54) PROCESS FOR THE SYNTHESIS OF PROGESTERONE RECEPTOR MODULATORS

(75) Inventors: Yanzhong Wu, Bardonia, NY (US); Bogdan Kazimierz Wilk, New City, NY (US); Zhixian Ding, Fort Lee, NJ (US); Xinxu Shi, Flushing, NY (US); Charles Chao Wu, Denville, NJ (US); Panolil Raveendranath, Monroe, NY (US); Haris Durutlic, New Windsor, NY (US)

(73) Assignee: Wyeth LLC, Madison, NJ (US)

( * ) Notice: Subject to any disclaimer, the term of this patent is extended or adjusted under 35 U.S.C. 154(b) by 725 days.

(21) Appl. No.: 11/494,425

(22) Filed: Jul. 27, 2006

(65) Prior Publication Data

US 2007/0027327 A1      Feb. 1, 2007

Related U.S. Application Data

(60) Provisional application No. 60/704,010, filed on Jul. 29, 2005.

(51) Int. Cl.
C07D 209/04  (2006.01)
(52) U.S. Cl. ........................................ 548/486; 548/484
(58) Field of Classification Search ................... 548/484, 548/486
See application file for complete search history.

(56) References Cited

U.S. PATENT DOCUMENTS

| | | |
|---|---|---|
| 5,973,165 A | 10/1999 | Kuo et al. |
| 2004/0186160 A1 | 9/2004 | Tang et al. |
| 2005/0239779 A1 | 10/2005 | Wilk et al. |
| 2005/0250766 A1 | 11/2005 | Wilk et al. |
| 2005/0272702 A1 | 12/2005 | Wilk et al. |
| 2006/0030615 A1 | 2/2006 | Fensome et al. |
| 2006/0030717 A1 | 2/2006 | Fensome et al. |
| 2006/0142355 A1* | 6/2006 | Singh et al. .................. 514/366 |
| 2006/0247441 A1 | 11/2006 | Wilk et al. |
| 2006/0247442 A1 | 11/2006 | Wilk et al. |

FOREIGN PATENT DOCUMENTS

| | | |
|---|---|---|
| JP | 2000239253 | 9/2000 |
| WO | WO-01/47884 A1 | 7/2001 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Kwon, Younggil. Handbook of Essential Pharmacokinetics, Pharmacodynamics and Drug Metabolism for Industrial Scientists. Jun. 24, 2001. p. 213, paragraph 3.*

Ettmayer, Peter, Medicinal Chemistry, Lessons Learned from Marketed and Investigational Prodrugs, 47(10) (2004) 2394-2404.*
Soledade et al., "Concise synthesis of the cruciferous phytoalexins brassilexin, sinalexin, wasalexins and analogues: expanding the scope of the Vilsmeier formulation", J. Org. Chem., 70:1828-1834 (Feb. 2, 2005).
Wilk et al., "A practical large-scale preparation of 5'-bromospiro(cyclohexane-1,3'-[3H]indol-2'-(1'H)-one", Org. Prep. Proced. Int., 37(3):283-285 (Jun. 2005).
Fensome et al., "New progesterone receptor antagonists: 3,3-disubstituted-5-aryloxindoles", Bioorg. Med. Chem. Lett., 12:3487-3490 (Dec. 2, 2002).
Adams, J., et al., Mapping the Kinase Domain of Janus Kinase 3, *Bioorganic & Medicinal Chemistry Letters*, 2003, pp. 3105-3110, vol. 13.
Crestini, C., et al., A New Efficient and Mild Synthesis of 2-Oxindoles by One-Pot Wolff-Kishner Like Reduction of Isatin Derivatives, *Synthetic Communications*, 1994, pp. 2835-2841, vol. 24(20).
Moody, C., et al., Dirhodium(II) tetraacetate catalyzed reactions of diazo thioamides: isolation and cycloaddition of anhydro-4-hydroxy-1,3-thiazolium hydroxides . . . , *Org. Biomol. Chem.*, Jul. 9, 2003, pp. 2716-2722, vol. 1.
Quintana, R., et al., Monomolecular films of compounds with potential dermophilic and prophylactic properties. Esters of dihydroxyacetone, *Canadian Journal of Chemistry*, 1969, pp. 853-856, vol. 47.
Robertson, D., et al., Dihydropyridazinone Cardiotonics: The Discovery and Inotropic Activity of 1,3-Dihydro-3,3-dimethyl-5-(1,4,5,6-tetrahydro-6-oxo-3-pyridazinyl)-2H-indol-2-one, *J. Med. Chem.*, 1986, pp. 1832-1840, vol. 29.
Soriano, D., et al., Example of the Wolff-Kishner Reduction Procedure Suitable for an Undergraduate Organic Lab Experiment, *J. Chem. Edu.*, 1993, p. 332, vol. 70(4).
Wenkert, E., et al., Raney Nickel-induced Alkylation Reactions, *Acta Chemica Scandinavia, Series B: Organic Chemistry and Biochemistry*, 1982, pp. 348-350, v. B36(5).
Beyersbergen Van Henegouwen, W., et al., First Total Synthesis of ent-Gelsedine via a Novel Iodide-Promoted Allen N-Acyliminium Ion Cyclization, *J. Org. Chem.*, Oct. 27, 2000, pp. 8317-8325, vol. 65(24).

* cited by examiner

*Primary Examiner*—Kamal A Saeed
*Assistant Examiner*—Samantha L Shterengarts
(74) *Attorney, Agent, or Firm*—Raquel M. Alvarez; Howson & Howson LLP

(57) ABSTRACT

Processes for preparing oxindoles, which can be utilized in the preparation of a variety of useful compounds, and methods for minimizing or preventing N-alkylation of amide containing compounds, including oxindoles, are provided. Also provided is a compound of the following structure:

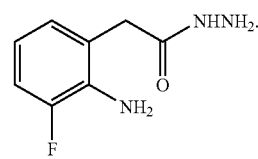

34 Claims, No Drawings

PROCESS FOR THE SYNTHESIS OF PROGESTERONE RECEPTOR MODULATORS

CROSS-REFERENCE TO RELATED APPLICATIONS

This application claims the benefit under 35 USC 119(e) of prior U.S. Provisional Patent Application No. 60/704,010, filed Jul. 29, 2005.

BACKGROUND OF THE INVENTION

The present invention relates to improved processes for preparing oxindoles and related amide containing compounds, and to useful intermediates thereof.

Several complicated routes to preparing 2-oxindoles are known in the art and include reaction of isatins with hydrazine (D. S. Soriano, J. Chem. Edu., 1992, 70:332 and Crestini, Synth. Commun., 1994, 24:2835). The Soriano route entails the use of expensive anhydrous ethanol as the solvent during the process and a tedious purification process, thereby making the process unfavorable to scale up. The Crestini route utilizes explosive pure hydrazine. Both methods require high temperatures (about 200° C.) and the yields are only moderate.

Another method of preparing 2-oxindoles utilizes a weak base such as sodium acetate as the catalyst, but the process includes boiling off a high boiling point solvent such as dimethylformamide (DMF), which is not practical in a large-scale synthesis (U.S. Pat. No. 5,973,165 and Japanese Patent Publication No. 2000239253).

A further route utilizes a catalyst such as diazabicyclooctane, diazabicycloundecene, ethyldiisopropylamine, or combinations thereof as the catalyst, but the yields are only moderate and the purification is complicated (Schwendinger et al., International Patent Publication No. 2001047884).

What is needed in the art are alternative processes for preparing 2-oxindoles that provide inexpensive reagents, high yields, and simple purifications, especially on a large scale.

SUMMARY OF THE INVENTION

In one aspect, processes for preparing 2-oxindoles are provided, including (a) combining an isatin and ethylene glycol; (b) reacting the solution of step (a) with aqueous hydrazine; and (c) isolating the 2-oxindole.

In another aspect, processes are provided for preparing a 2-oxindole of the structure:

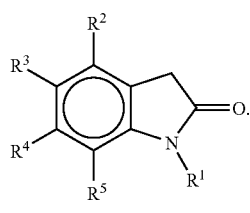

In a further aspect, a compound of the structure:

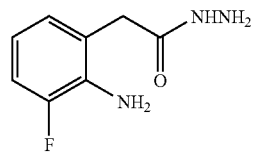

is provided.

In yet another aspect, processes are provided for preparing 7-fluoro-2-oxindole, including reacting an acid with a compound of the structure:

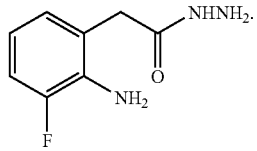

In still a further aspect, methods are provided for preventing or minimizing N-alkylation of linear or cyclic amide compounds.

In another aspect, methods are provided for preventing or minimizing N-alkylation of oxindoles.

Other aspects and advantages will be readily apparent from the following detailed description of the invention.

DETAILED DESCRIPTION OF THE INVENTION

A more efficient route to preparing 2-oxindoles, as compared to the processes in the art, is provided. Specifically, 2-oxindoles can be prepared using inexpensive reagents, and simple purifications. These yields are also obtained in the preparation of 2-oxindoles on a large scale. See, Scheme 1.

Scheme 1

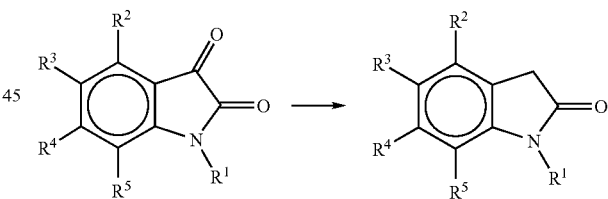

The 2-oxindoles prepared can be utilized to prepare other 2-oxindole related compounds including alkylated 2-oxindoles, brominated 2-oxindoles, and 2-oxindoles coupled with other compounds, e.g. 2-oxindoles coupled with aryl and heteroaryl compounds, among others. See, Scheme 2.

Scheme 2

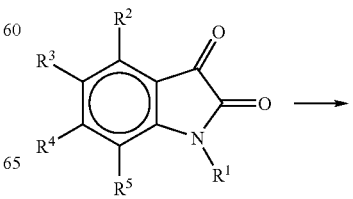

-continued

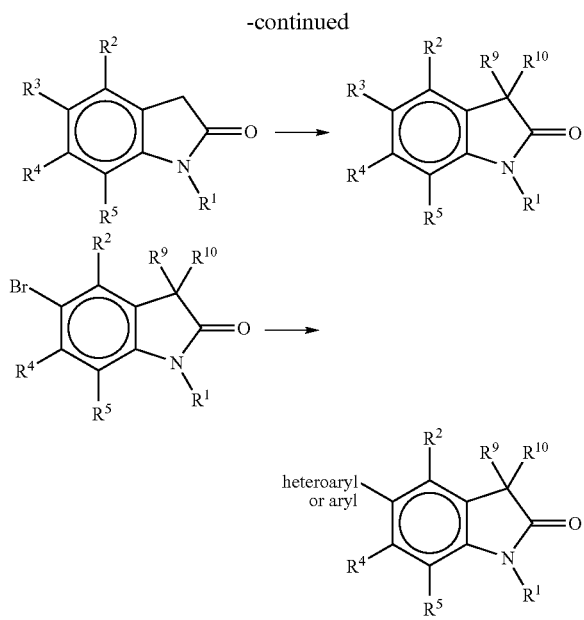

A variety of oxindoles can be prepared as described herein and includes 2-oxindoles, and in one embodiment 2-oxindoles of the structure:

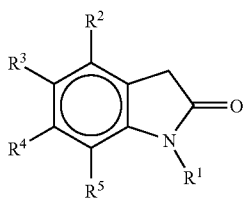

wherein, $R^1$ is selected from among H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl; $R^2$, $R^3$, $R^4$, and $R^5$ are independently selected from among hydrogen, halogen, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or $R^2$ and $R^3$; $R^3$ and $R^4$; $R^4$ and $R^5$; or $R^5$ and $R^1$ are fused to form (i) a 3 to 9 membered carbon-based saturated or unsaturated ring; or (ii) a 3 to 9 membered heterocyclic ring containing in its backbone one to three heteroatoms selected from among O, S and N; wherein rings (i)-(ii) are optionally substituted by 1 to 3 groups selected from among $C_1$ to $C_6$ alkyl, substituted $C_1$, to $C_6$ alkyl, halogen, $C_1$ to $C_6$ alkoxy, substituted $C_1$, to $C_6$ alkoxy, and $N(R^8)_2$; $R^6$ is selected from between $C_1$ to $C_6$ alkyl or substituted $C_1$ to $C_6$ alkyl; $R^7$ is selected from among H, $C_1$, to $C_6$ alkyl, substituted $C_1$ to $C_6$ alkyl, and $CF_3$; and $R^8$ is selected from among $C_1$, to $C_6$ alkyl, $C_1$, to $C_6$ substituted alkyl, $C_1$, to $C_6$ alkoxy, and substituted $C_1$, to $C_6$ alkoxy.

The term "alkyl" is used herein to refer to both straight- and branched-chain saturated aliphatic hydrocarbon groups. In one embodiment, an alkyl group has 1 to about 8 carbon atoms. In another embodiment, an alkyl group has about 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, $C_4$).

The term "cycloalkyl" is used herein to refer to cyclic, saturated aliphatic hydrocarbon groups. In one embodiment, a cycloalkyl group has 3 to about 8 carbon atoms. In another embodiment, a cycloalkyl group has about 3 to about 6 carbon atoms (i.e., $C_3$, $C_4$, $C_5$ or $C_6$).

The term "alkenyl" is used herein to refer to both straight- and branched-chain alkyl groups with at least one carbon-carbon double bond. In one embodiment, an alkenyl group contains 2 to about 8 carbon atoms. In another embodiment, an alkenyl group contains 2 to about 6 carbon atoms.

The term "alkynyl" is used herein to refer to both straight- and branched-chain alkyl groups with at least one carbon-carbon triple bond. In one embodiment, an alkynyl group has 2 to about 8 carbon atoms. In another embodiment, an alkynyl group has 2 to about 6 carbon atoms. In yet another embodiment, an alkynyl group has 1 or 2 carbon-carbon triple bonds and 3 to about 8, or in another embodiment 3 to about 6, carbon atoms.

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic, substituted aryl, substituted heterocyclic, alkoxy, aryloxy, alkoxy, alkylcarbonyl, alkylcarboxy, alkylamino, or arylthio. These substituents may be attached to any carbon of an alkyl, alkenyl, alkynyl or cycloalkyl group provided that the attachment constitutes a stable chemical moiety.

The term "acyl" as used herein refers to a carbonyl substituent, i.e., a C(O)(R) group where R is a straight- or branched-chain saturated aliphatic hydrocarbon group including, without limitation, alkyl, alkenyl, and alkynyl groups. In one embodiment, the R groups have 1 to about 8 carbon atoms. In another embodiment, the R groups have 1 to about 6 carbon atoms. The term "substituted acyl" refers to an acyl group which is substituted with 1 or more groups including halogen, CN, OH, and $NO_2$.

The term "aryl" is used herein to refer to an aromatic carbocyclic system, e.g. of 6-14 carbon atoms, which can include a single ring or multiple aromatic rings fused or linked together such that at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio. In one embodiment, a substituted aryl group is substituted with 1 to about 4 substituents.

The terms "heterocycle" and "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring contains from 1 to 4 heteroatoms in the backbone of the ring. When present in the backbone of the heterocycle, the nitrogen and sulfur atoms may be oxidized. The terms "heterocycle" and "heterocyclic" also refers to any multicyclic ring in which any of the above defined heterocyclic rings is fused to an aryl ring, e.g., of 6 to 14 carbon atoms. The heterocyclic ring may be attached at any heteroatom or carbon atom provided the resultant structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains from 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaromatic ring is fused to an aryl ring. The heteroaromatic ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, azepinyl, triazinyl, thienyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio. A substituted heterocycle or heteroaryl group may have 1, 2, 3, or 4 substituents.

The term "arylthio" as used herein refers to the S(aryl) group, where the point of attachment is through the sulfur-atom, and the aryl group can be substituted as noted above.

The term "alkoxy" is used herein to refer to the O(alkyl) group, where the point of attachment is through the oxygen atom and the alkyl group can be substituted as noted above.

The term "aryloxy" is used herein to refer to the O(aryl) group, where the point of attachment is through the oxygen atom and the alkyl group can be substituted as noted above.

The term "alkylcarbonyl" is used herein to refer to the C(O)(alkyl) group, where the point of attachment is through the carbon atom of the carbonyl moiety and the alkyl group can be substituted as noted above.

The term "alkylcarboxy" is used herein to refer to the C(O)O(alkyl) group, where the point of attachment is through the carbon atom of the carboxy moiety and the alkyl group can be substituted as noted above.

The term "alkylamino" refers to both secondary and tertiary amines where the point of attachment is through the nitrogen atom and the alkyl groups can be substituted as noted above. The alkyl groups can be the same or different.

The term "halogen" refers to Cl, Br, F, or I.

The compounds described herein can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The compounds described herein can also encompass tautomeric forms of the structures provided herein characterized by the bioactivity of the drawn structures. Further, the compounds described herein can be used in the form of salts derived from pharmaceutically or physiologically acceptable acids or bases.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. Salts may also be formed from inorganic bases, desirably alkali metal salts, for example, sodium, lithium, or potassium, and organic bases, such as ammonium, mono-, di-, and trimethylammonium, mono-, di- and triethylammonium, mono-, di- and tripropyl-ammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts.

These salts, as well as other compounds described herein, can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds discussed herein also encompass "metabolites" which are unique products formed by processing the compounds described herein by the cell or patient. In one embodiment, metabolites are formed in vivo.

The first step in the process of preparing the 2-oxindoles includes combining an isatin and ethylene glycol. In one embodiment, the 2-oxindole dissolves in the ethylene glycol. In another embodiment, the 2-oxindole does not dissolve in the ethylene glycol. Typically, the isatin is a compound of the structure:

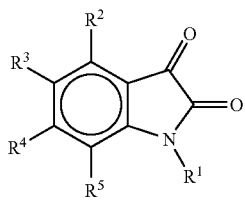

wherein, $R^1$ to $R^5$ are defined above. In one embodiment, the isatin is 7-fluoroisatin.

The amount of ethylene glycol that is combined with the isatin can readily be determined by one of skill in the art. However, in one embodiment the ratio of ethylene glycol to isatin is about 2 to about 10 mL of ethylene glycol to about 1 gram of isatin. In one embodiment, the ratio of ethylene glycol to isatin is about 2 mL of ethylene glycol to about 1 gram of isatin. In another embodiment, the ratio of ethylene glycol to isatin is about 5 mL of ethylene glycol to about 1 gram of isatin.

Once the isatin is combined with the ethylene glycol in the appropriate ratio, the 2-oxindole is reduced using aqueous hydrazine, typically an excess of hydrazine. In one embodiment, the ratio of hydrazine to isatin is about 1.5 to 3 equivalents of hydrazine to about 1 equivalent of isatin, and in a further embodiment about 2 equivalents of hydrazine to about 1 equivalent of isatin. The reaction to form the 2-oxindole is typically completed in about 4 to about 8 hours. However, the reduction reaction is not so limited and may be longer or shorter than the noted time period. In one embodiment, the reaction temperature is between about 110 to about 140° C., and in a further embodiment is about 120° C.

Once prepared, the 2-oxindole can be isolated and purified using techniques known to those of skill in the art including extraction, filtration, distillation, chromatography, and crystallization, among others. The particular route of isolating and purifying the 2-oxindole should not be considered a limitation. In one embodiment, the 2-oxindole is precipitated using water and is isolated by filtration. The typical yield of this step is about 81 to 86%.

During preparation of the 2-oxindoles described herein, impurities can be formed. Typically, impurities of the following structure are formed:

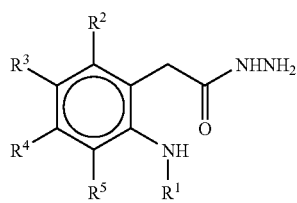

wherein, $R^1$ to $R^5$ are defined above. In one embodiment, an impurity of the following structure is formed:

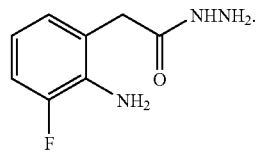

These impurities can be converted to the 2-oxindole described herein using an inorganic acid. See, Scheme 3, where $R^1$ to $R^5$ are defined above. A number of inorganic acids can be utilized for this purpose and include hydrochloric acid, hydrobromic acid, sulfuric acid, nitric acid, phosphoric acid, and perchloric acid, among others.

Scheme 3

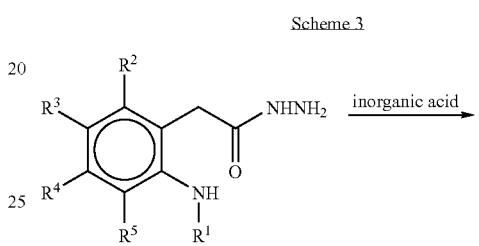

In one embodiment, the impurity is converted to 7-fluoro-2-oxinole according to Scheme 4.

Scheme 4

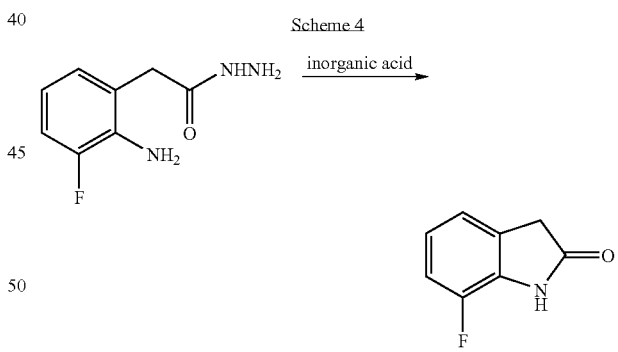

Once prepared the 2-oxindole can be alkylated at the 3-position to form a compound of the following structure:

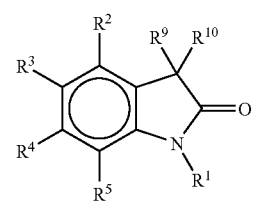

wherein, $R^1$ to $R^5$ are defined above, $R^9$ is $C_1$ to $C_6$ alkyl or $C_1$ to $C_6$ substituted alkyl; and $R^{10}$ is H, $C_1$ to $C_6$ alkyl, $C_1$ to $C_6$ substituted alkyl, or $CF_3$.

Alkylation of 2-oxindoles can be quite complicated when the N-atom of the indole at the 1-position is substituted with a H-atom or a group that is easily displaced. Typically, N-alkylation at the 1-position occurs in addition to alkylation at the 3-position to produce a di- or tri-alkylated compound instead of a mono- or di-alkylated compound. See, e.g., Robertson (J. Med. Chem. (1986), 29(10):1832-40) and Winfred (J. Org. Chem. (2000), 65(24):8317-8325). Therefore, a method to eliminate or reduce N-alkylation to predominantly afford the 2-oxindole alkylated at the 3-position is provided.

When CuX (X is I, Br, Cl) or the $CuBr.Me_2S$ (i.e., $CuBr(CH_3)_2S$) complex are utilized in the presence of an alkyl halide during alkylation, N-alkylation can be prevented or very efficiently inhibited when the reaction is performed at low temperatures, as described in detail below. See, Scheme 5. In one embodiment, N-alkylation was reduced to a 98:2 or greater ratio of dialkylation:trialkylation resulting in at least a 98:2 ratio of dialkylated 2-oxindole to trialkylated 2-oxindole. In a further embodiment, a 98:2 ratio of dialkylation:trialkylation occurred during alkylation resulting in a 98:2 ratio of dialkylated 2-oxindole to trialkylated 2-oxindole. In another embodiment, a 98:1 ratio of dialkylation:trialkylation occurred during alkylation resulting in a 98:1 ratio of dialkylated 2-oxindole to trialkylated 2-oxindole.

Scheme 5

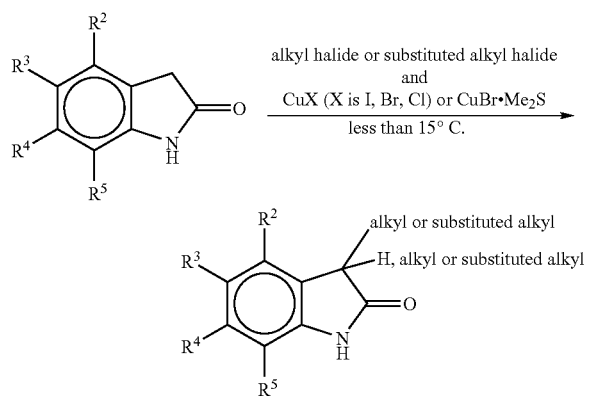

Alkylation of the 2-oxindole is typically performed using an alkyl halide. The alkylation is performed in the presence of a copper halide or a copper halide adduct and a base. In one embodiment, the copper halide or copper halide adduct is utilized at an amount of about 0.05 to about 1 equivalents with respect to the 2-oxindole, in a further embodiment at an amount of about 0.1 equivalent. In one embodiment, the copper halide is CuI, CuBr, or CuCl and the copper halide adduct is $CuBr.(CH_3)_2S$. The base is in one embodiment a butoxide, in a further embodiment potassium or sodium t-butoxide, and in still a further embodiment potassium t-butoxide. An excess of the base is utilized in an amount of about 3 to about 6 equivalents, and more desirably about 5 equivalents. The alkylation can be performed in a variety of solvents which can readily be selected by one of skill in the art. In one embodiment, the solvent is an ether, in a further embodiment is tetrahydrofuran (THF) or dimethoxyethane (DME), and in still a further embodiment is THF.

The inventors have also found that the temperature at which the alkylation is performed is critical to prevention or inhibition of N-alkylation and thereby formation of the trialkylated by-product. If a temperature of higher than about 15° C. is utilized, a significant amount of N-alkylation occurs, thereby producing the trialkylated by-product. In one embodiment, a temperature of about 0 to about 15° C. and in a further embodiment about 6 to about 12° C. is maintained during alkylation.

The alkyl halide can be any carbon length halide, e.g., a $C_1$ to $C_8$ alkyl halide, such as methyl, ethyl, propyl, and butyl iodide, and in a further embodiment is methyl iodide. In one embodiment, the alkyl halide is utilized in excess. In a further embodiment, an excess of greater than about 2 equivalents of the alkylating agent to the 2-oxindole, in yet a further embodiment about 2 to about 2.5 equivalents, and in still a further embodiment about 2.2 equivalents is utilized.

The alkylated 2-oxindole can be isolated and purified using techniques known to those of skill in the art including extraction, filtration, distillation, chromatography, and crystallization, among others. The particular route of isolating and purifying the 2-oxindole should not be considered a limitation. In one embodiment, the alkylated 2-oxindole is isolated by quenching the alkylation, in a further embodiment with ammonium chloride; extracting the alkylated 2-oxindole, in a further embodiment using a solvent with a polarity similar to t-butyl methyl ether, in still a further embodiment using t-butyl methyl ether; removing the solvent using a technique such as distillation; and removing residual water from the product, in a further embodiment through the use of acetic acid. The alkylated 2-oxindole is generally stored in about 5 to about 8 parts (g/mL) acetic acid.

Bromination of 2-oxindole is then performed as described in Adams (Bioorganic & Med. Chem. Lett. (2003), 13(18): 3105-3110) to prepare the corresponding brominated 2-oxindole. In one embodiment, a 4-, 5-, 6-, or 7-bromine substituted 2-oxindole, and in a further embodiment a 2-oxindole of the structure below, wherein $R^1$, $R^2$, $R^4$, $R^5$, $R^9$ and $R^{10}$ are as defined above, is prepared.

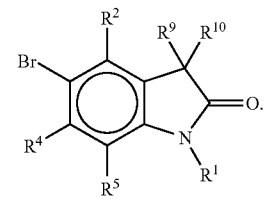

In the bromination step, bromine is slowly added to the alkylated 2-oxindole at room temperature in a solvent that does not react with bromine. In one embodiment, the bromination step is performed in acetic acid or dichloromethane, among others. One of skill in the art would readily be able to determine a suitable solvent to utilize in the bromination step. Upon completion of the reaction, the reaction is quenched, typically using aqueous sodium bisulfite, among others, and the crude compound is isolated and dried using techniques known to those of skill in the art. Typically, the brominated compound is collected using filtration. The crude compound can be further purified by dissolution in ethyl acetate and filtering through a pad of silica gel. The purified brominated compound is then precipitated using heptane.

The brominated 2-oxindole can then be coupled with a coupling reagent to prepare 4-, 5-, 6-, or 7-substituted oxindoles. In one embodiment, the procedure set forth in US Patent Application Publication No. US-2005-0272702-A1 (Wilk, et al.), published Dec. 8, 2005, is utilized to couple the brominated 2-oxindole with a coupling reagent. In another embodiment, the brominated 2-oxindole is coupled at the 5-position. The brominated 2-oxindole is typically coupled with alkyl, aryl, or heteroaryl coupling reagents, and in one embodiment with aryl and heteroaryl coupling reagents. The coupling is performed in the presence of a palladium (Pd) catalyst, in one embodiment a Pd(0) catalyst, using at least a 1% mol equivalent of the Pd catalyst as compared to the brominated 2-oxindole and with a weak base. Dichloro bis (triphenylphosphine) palladium (II) is the preferred catalyst since the coupling can be performed at a reduced temperature. In one embodiment, the brominated 2-oxindole is coupled with an optionally substituted cyanopyrrole. In another embodiment, the brominated 2-oxindole is coupled with [1,3,6,2]dioxazaborcan-2-yl-1-methyl-1H-pyrrole-2-carbonitrile.

The coupling can be performed using any solvent, which can readily be determined by one of skill in the art. Typically, solvents such as THF or 1,2-dimethoxyethane can be utilized, optionally with water, e.g., about 1 to about 5 parts of water. In one embodiment, the coupling is performed at a temperature of about 55 to about 82° C., and in a further embodiment about 65° C. The weak base can also be selected by one of skill in the art and is typically sodium or potassium carbonate. An equimolar or slight excess of the base is typically utilized and is in one embodiment about 1.0 to about 1.5 equivalents, and in a further embodiment about 1.2 equivalents. The coupling is generally complete in about 2 to about 3 hours, however, the reaction is not so limited and may take less or more time to complete. The coupled 2-oxindole is then isolated using techniques known to those of skill in the art. Alternatively, the coupled 2-oxindole is retained in the solution. In one embodiment, the coupling is quenched using about 10 parts of brine and the organic phase is separated.

After extraction of the coupled 2-oxindole in the organic layer, residual Pd is removed as described in Christine (Adv. Synth. Catal. (2004) 346:889-900) which provides methods of using N-acetyl-L-cysteine to remove Pd. The inventors have found that by adding about 0.025 to about 0.50 equivalents, or in a further embodiment about 0.1 equivalents, of N-acetyl-L-cysteine to the organic layer containing the coupled 2-oxindole, the residual palladium is removed. Any residual solid palladium can be removed by filtration using techniques known to those of skill in the art. In one embodiment, the filtration is performed using a charcoal and a Celite® reagent pad. Alternatively, any palladium complex that is soluble in the solution is removed by recrystallization as described below. In one embodiment, the organic layer is refluxed with the cysteine for about 1 hour, filtered through a charcoal and a Celite® reagent pad, the filtrate is concentrated using techniques known to those of skill in the art, and the solvent is replaced with about 6 to about 7 parts of ethanol, typically using distillation. The coupled compound is then crystallized, the solid isolated using techniques known to those of skill in the art such as filtration, the collected solid washed with ethanol, and the washed solid dried at about 45 to about 55° C. under vacuum to give the final compound.

In one embodiment, a process is provided for preparing a 2-oxindole, including (a) combining about 2 mL ethylene glycol:about 1 g of an isatin of the structure:

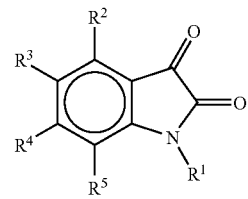

wherein, $R^1$ is selected from among H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl; $R^2$, $R^3$, $R^4$, and $R^5$ are independently selected from among H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or $R^2$ and $R^3$; $R^3$ and $R^4$; $R^4$ and $R^5$; or $R^5$ and $R^1$ are fused to form (i) a 3 to 9 membered carbon-based saturated or unsaturated ring; or (ii) a 3 to 9 membered heterocyclic ring containing in its backbone one to three heteroatoms selected from the group consisting of O, S and N; wherein rings (i)-(ii) are optionally substituted by 1 to 3 groups selected from among $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$; $R^6$ is selected from between $C_1$ to $C_6$ alkyl and $C_1$ to $C_6$ substituted alkyl; $R^7$ is selected from among H, $C_1$ to $C_6$ alkyl, $C_1$ to $C_6$ substituted alkyl, and $CF_3$; and $R^8$ is selected from among $C_1$ to $C_6$ alkyl, $C_1$ to $C_6$ substituted alkyl, $C_1$ to $C_6$ alkoxy, and substituted $C_1$ to $C_6$ alkoxy; (b) reacting the solution of step (a) with about 2 equivalents of aqueous hydrazine; and (c) isolating the 2-oxindole of the structure:

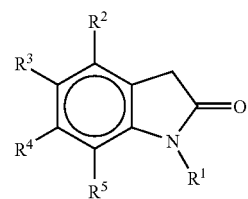

wherein, $R^1$ to $R^5$ are defined above.

In a further embodiment, a process is provided for preparing an aryl substituted 2-oxindole, including (a) combining about 2 mL ethylene glycol:about 1 g of an isatin of the structure:

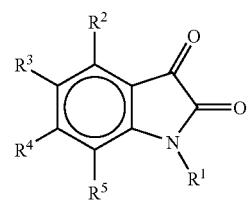

wherein $R^1$-$R^5$ are as defined above; (b) reacting the solution of step (a) with about 2 equivalents of aqueous hydrazine to form a 2-oxindole of the structure:

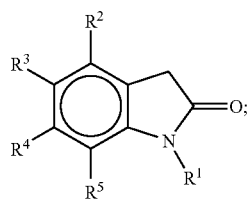

(c) alkylating the 2-oxindole with an alkyl halide in the presence of a copper halide or a copper halide adduct to form an alkylated 2-oxindole of the structure:

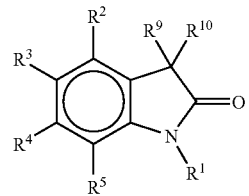

wherein, $R^9$ is $C_1$ to $C_6$ alkyl or $C_1$ to $C_6$ substituted alkyl; and $R^{10}$ is H, $C_1$ to $C_6$ alkyl, $C_1$ to $C_6$ substituted alkyl, or $CF_3$; (d) brominating the alkylated 2-oxindole; (e) coupling the brominated 2-oxindole with an aryl compound in the presence of a palladium catalyst; and (f) reducing the content of palladium or palladium compounds in the product of step (e) using N-acetyl-L-cysteine.

In another embodiment, a process is provided for preparing a 2-oxindole of the structure:

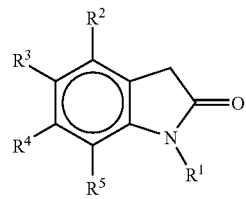

wherein $R^1$-$R^5$ are as defined above; or a pharmaceutically acceptable salt, tautomer, metabolite or prodrug thereof. The process includes reacting an inorganic acid and a compound of the following structure:

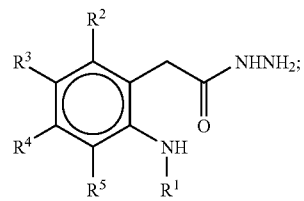

or a pharmaceutically acceptable salt, tautomer, metabolite or prodrug thereof.

In still a further embodiment, a process is provided for preparing 5-(7-Fluoro-3,3-dimethyl-2-oxo-2,3-dihydro-1H-indol-5-yl)-1-methyl-1H-pyrrole-2-carbonitrile including reacting 7-fluoro-1H-indole-2,3-dione and aqueous hydrazine in ethylene glycol to form the 2-oxindole; alkylating the 2-oxindole at the 3-position; brominating the alkylated 2-oxindole; reacting the brominated 2-oxindole with 5-[1,3,6,2]dioxazaborocan-2-yl-1-methyl-1H-pyrrole-2-carbonitrile, sodium carbonate, and $PdCl_2(PPh_3)_2$; removing residual $PdCl_2(PPh_3)_2$ or a by-product thereof using N-acetyl-L-cysteine; and isolating 5-(7-Fluoro-3,3-dimethyl-2-oxo-2,3-dihydro-1H-indol-5-yl)-1-methyl-1H-pyrrole-2-carbonitrile. See, Scheme 6.

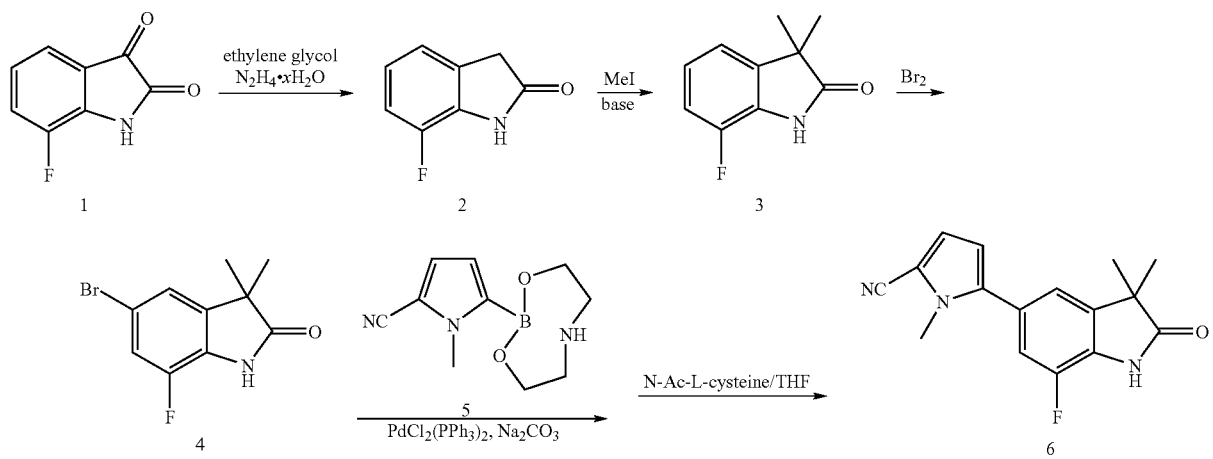

Scheme 6

In still a further embodiment, a process is provided for preparing 5-(7-fluoro-3,3-dimethyl-2-oxo-2,3-dihydro-1H-indol-5-yl)-1-methyl-1H-pyrrole-2-carbonitrile, including reacting 7-fluoro-1H-indole-2,3-dione and aqueous hydrazine in ethylene glycol to form the 2-oxindole; brominating the 2-oxindole; reacting the 2-oxindole with 5-[1,3,6,2]dioxazaborocan-2-yl-1-methyl-1H-pyrrole-2-carbonitrile, sodium carbonate, and $PdCl_2(PPh_3)_2$; removing residual $PdCl_2(PPh_3)_2$ or a by-product thereof using N-acetyl-L-cysteine; and isolating 5-(7-Fluoro-3,3-dimethyl-2-oxo-2,3-dihydro-1H-indol-5-yl)-1-methyl-1H-pyrrole-2-carbonitrile.

In yet another embodiment, a process is provided for preparing 7-fluoro-2-oxindole, including reacting an inorganic acid with a compound of the following structure:

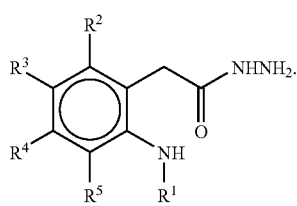

In still a further embodiment, a method is provided for preventing or minimizing N-alkylation of an oxindole, including alkylating the oxindole with an alkyl halide in the presence of a copper halide or $CuBr.Me_2S$ at a temperature less than about 15° C. In one embodiment, the copper halide is copper iodide, copper bromide, or copper chloride. In another embodiment, the method provides less than about 2% of N-alkylation.

Methods of Minimizing N-Alkylation of Amide Containing Compounds

Alkylation of compounds containing amide groups can be quite complicated when the N-atom of the amide group is unprotected. Typically, during alkylation of a carbon atom adjacent to a carbonyl group of an amide group, the N-atom is alkylated as well as the carbon-atom to form a tri-alkylated product. This is particularly a problem when the N-atom of the amide is substituted with an H-atom or a group that is easily displaced with the alkyl group, i.e., the N-atom is unprotected. A method is thus provided to eliminate or reduce N-alkylation of the amide to predominantly afford a product whereby the carbon-atom adjacent to the carbonyl group is alkylated.

The alkylation described herein can be performed on compounds containing an amide group, whereby the alkylation occurs at the carbon atom that is directly adjacent to the carbonyl group. In one embodiment, the alkylation is performed on linear amides. In another embodiment, the alkylation is performed on cyclic amides. See, Scheme 7.

Scheme 7

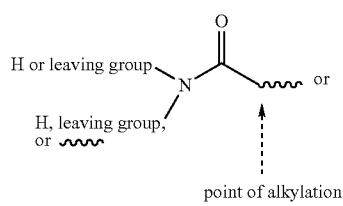

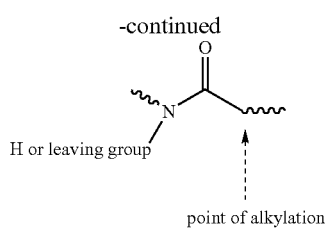

In one embodiment, methods are provided for preventing or reducing N-alkylation of cyclic compounds containing amide functional groups, whereby one or more points of the amide group is bound to another unreactive group. Also provided is minimizing or preventing alkylation of 2-pyrrolidone, 1,4-oxazin-2-ones, 1,4-benzoxazin-2-ones, indol-2-one, and quinolin-2-one compounds by preventing or minimizing N-alkylation. For example, N-alkylation can be prevented or minimized when alkylating the compounds of the following structures:

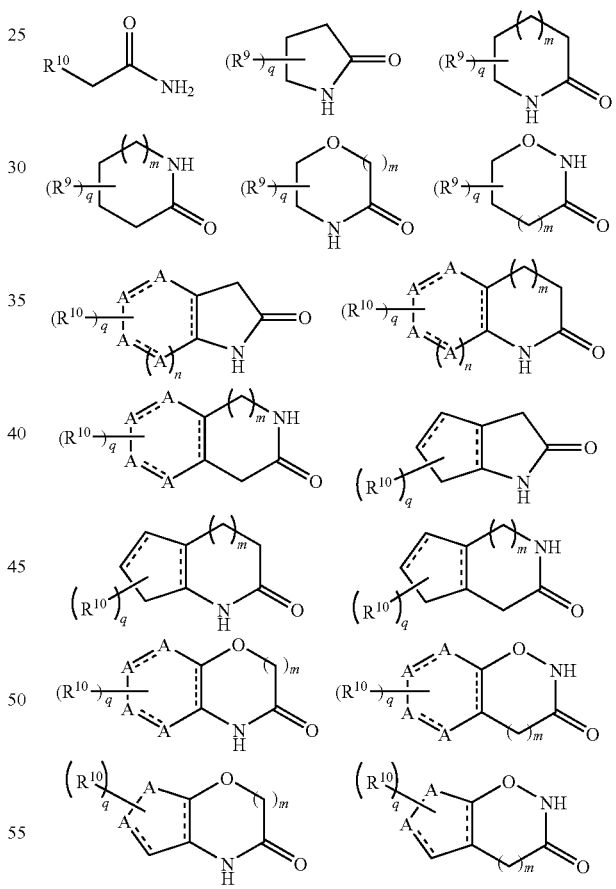

wherein:

A is $CH$, $CH_2$, $CR_{10}$, or $C(R_{10})_2$ or N, with the proviso that when A is N, the bond attached thereto is unsaturated;

$R^9$ is attached at any position on the ring and is aryl, substituted aryl, heterocycle, substituted heterocycle, heteroaryl, substituted heteroaryl, alkyl, or substituted alkyl, with the proviso that $R^9$ is not attached to the C-atom adjacent to the carbonyl;

$R^{10}$ is aryl, substituted aryl, heterocycle, substituted heterocycle, heteroaryl, substituted heteroaryl, alkyl, or substituted alkyl; $R^{10}$ may be bound to an A;

$R^9$ or $R^{10}$ is an optionally substituted unsaturated or saturated ring fused to the -A-A-A-A-moiety, with the proviso that $R^9$, $R^{10}$, and the ring substituents are not alkylated; and m, n, and q are, independently, 1 to 5.

The alkylation is performed using CuX (X is I, Br, Cl) or the CuBr.Me$_2$S complex in the presence of an alkyl halide at low temperatures. In one embodiment, N-alkylation is reduced to a 98:2 or greater ratio of dialkylation:trialkylation resulting in at least a 98:2 ratio of dialkylated 2-oxindole to trialkylated product.

In one embodiment, the alkylation is performed in the presence of a copper halide or a copper halide adduct and a base. The alkyl halide can be any carbon length halide, such as methyl, ethyl, propyl, and butyl iodide, and in one embodiment is methyl iodide. In a further embodiment, the alkyl halide is utilized in excess. In a further embodiment, an excess of greater than about 2 equivalents of the alkylating agent to the unalkylated reagent, about 2 to about 2.5 equivalents, or about 2.2 equivalents is utilized.

In another embodiment, the copper halide or copper halide adduct is utilized at an amount of about 0.05 to about 1 equivalents to the unalkylated starting material, and in one embodiment about 0.1 equivalent. In one embodiment, the copper halide is CuI, CuBr, or CuCl and the copper halide adduct is CuBr.(CH$_3$)$_2$S. In one embodiment, the base is a butoxide, in a further embodiment potassium or sodium t-butoxide, and in still another embodiment potassium t-butoxide. An excess of the base is utilized in an amount of about 3 to about 6 equivalents, and in one embodiment about 5 equivalents. The alkylation can be performed in a variety of solvents which can readily be selected by one of skill in the art. In one embodiment, the solvent is an ether, in a further embodiment tetrahydrofuran (THF) or dimethoxyethane (DME), and in still a further embodiment THF.

The temperature at which the alkylation is performed is critical to prevention or inhibition of N-alkylation and thereby formation of the trialkylated by-product. If a temperature of higher than about 15° C. is utilized, a significant amount of N-alkylation occurs, thereby producing the trialkylated by-product. In one embodiment, a temperature of about 0 to about 15° C. or in a further embodiment about 6 to about 12° C. is maintained during alkylation. In another embodiment, the method provides less than about 2% of N-alkylation.

The following examples are illustrative only and are not intended to be a limitation on the present invention.

EXAMPLES

Example 1

Preparation of 7-Fluoro-1,3-dihydroindol-2-one

To a mixture of 7-fluoro-1H-indole-2,3-dione (100 g, 0.606 mol) in ethylene glycol (500 mL) was added an aqueous hydrazine solution (54% wt, 73 g, 1.21 mol) dropwise over 30 minutes. The mixture was heated to 120° C. and stirred for 6 hours. The mixture was cooled to room temperature and water (500 mL) was added. Concentrated hydrochloric acid (HCl; 60 mL) was added, the mixture was warmed to about 35 to about 40° C., and the mixture was stirred for 1 hour. The mixture was then cooled to about 0 to about 5° C. The solid compound was filtered, washed with cold water and dried at 55° C. under vacuum to give an off-white solid (76 g) in 83% yield with 96% HPLC purity.

Example 2

Preparation of 5-Bromo-7-fluoro-3,3-dimethyl-1,3-dihydro-indol-2-one

To a stirred slurry of potassium t-butoxide (t-BuOK-370 g, 3.30 mol) in tetrahydrofuran (THF; 1300 mL) was added a slurry of 7-fluoro-1,3-dihydroindol-2-one (100 g, 0.660 mol) in THF (1000 mL), followed by the addition of CuBrMe$_2$S (14 g, 0.070 mol). Methyl iodide (260 g, 1.83 mol) was then added dropwise to the mixture at about 5 to about 15° C. The reaction mixture was stirred for at least 20 minutes at 25° C. A solution of 24% ammonium chloride (NH$_4$Cl-141 g, 2.64 mol) in water (600 mL) was added to the reaction mixture. The organic layer was separated and washed with water (700 mL). The combined aqueous washes were extracted with t-butyl methylether (1000 mL). The combined organic layers are washed with brine (600 mL) and then concentrated by distillation. Acetic acid (869 mL) was then added and the mixture was concentrated under atmosphere pressure to a volume of about 650 mL.

To the stirred acetic acid solution, bromine (211 g, 1.32 mol) was added dropwise at about 25 to about 30° C. The reaction mixture was stirred for at least 1 hour at 25° C. and a solution of NaHSO$_3$ (103 g, 0.99 mol) in water (1500 mL) was added. The product was filtered and washed with water (800 mL) and MeOH (150 mL). The filtered solid was dried by suction to give a crude solid (150 g). The crude solid (110 g) was dissolved in ethyl acetate (1100 mL) to give a solution which was filtered through a silica gel pad (110 g) and the filtrate was concentrated to about 300 mL. Heptane (2500 mL) was added and the mixture was concentrated to a volume of about 1700 mL. The solid was collected by filtration, washed with 10% ethyl acetate in heptane, and dried to give a beige solid (99 g, 0.383 mol, 79% overall yield for methylation and bromination steps).

Example 3

Preparation of 5-(7-Fluoro-3,3-dimethyl-2-oxo-2,3-dihydro-1H-indol-5-yl)-1-methyl-1H-pyrrole-2-carbonitrile A mixture of 5-bromo-7-fluoro-3,3-dimethyl-1,3-dihydro-indol-2-one (100 g, 0.387 mole), 5-[1,3,6,2]Dioxazaborocan-2-yl-1-methyl-1H-pyrrole-2-carbonitrile (110 g, 0.252 mole), sodium carbonate (Na$_2$CO$_3$; 49.2 g, 0.233 mol), THF (2 L), water (0.5 L), and PdCl$_2$(PPh$_3$)$_2$(2.72 g, 3.9 mmol) was heated to 65° C. for 2 hours. The solution was then cooled to room temperature and a saturated sodium chloride solution (1.0 L) was added.

The organic phase was then isolated, N-acetyl-L-cysteine (31.7 g, 0.194 mol) was added, the mixture was heated to 65° C. for 1 hour and then cooled to room temperature. The cooled mixture was filtered through a glass-sintered funnel packed with the Celite® reagent (100 g) and charcoal (50 g). The filtrate was concentrated by distillation to a volume of about 300 mL and ethanol (EtOH; 500 mL) was added to the slurry. The mixture was distilled to a volume of about 400 mL and then cooled to about 20 to about 25° C. The solid was filtered, washed with ethanol, and dissolved in acetone (2.0 L) at 55° C. The resultant solution was filtered at about 40 to about 50° C. and then concentrated to a volume of about 200 mL. EtOH (1.0 L) was added and the mixture was concentrated to a volume of about 400 mL. The concentrated mixture was then cooled to about 5° C., the precipitated solid filtered, washed with ethanol and dried through vacuum to give a white solid (92.7 g, 84.3% yield with 99% HPLC purity).

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A process for producing an oxindole of the structure:

wherein

R$^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

R$^2$, R$^3$, R$^4$, and R$^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, OR$^6$, N(R$^7$)$_2$, CON(R$^7$)$_2$, SO$_2$N(R$^7$)$_2$, and COOH; or R$^2$ and R$^3$; R$^3$ and R$^4$; R$^4$ and R$^5$; or R$^5$ and R$^1$ are fused to form:

(i) a 3 to 9 membered carbon-based saturated or unsaturated ring; or (ii) a 3 to 9 membered heterocyclic ring containing in its backbone one to three heteroatoms selected from the group consisting of O, S and N;

wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and N(R$^8$)$_2$;

R$^6$ is selected from the group consisting of $C_1$ to $C_6$ alkyl and $C_1$ to $C_6$ substituted alkyl;

each R$^7$ is independently selected from the group consisting of H, $C_1$ to $C_6$ alkyl, $C_1$ to $C_6$ substituted alkyl, and CF$_3$; and each R$^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

said process comprising:

(a) reacting aqueous hydrazine and an isatin in ethylene glycol, wherein said isatin is of the following structure:

wherein:

R$^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

R$^2$, R$^3$, R$^4$, and R$^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, OR$^6$, N(R$^7$)$_2$, CON(R$^7$)$_2$, SO$_2$N(R$^7$)$_2$, and COOH; or R$^2$ and R$^3$; R$^3$ and R$^4$; R$^4$ and R$^5$; or R$^5$ and R$^1$ are fused to form:

(i) a 3 to 9 membered carbon-based saturated or unsaturated ring; or (ii) a 3 to 9 membered heterocyclic ring containing in its backbone one to three heteroatoms selected from the group consisting of O, S and N;

wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and N(R$^8$)$_2$;

R$^6$ is selected from the group consisting of $C_1$ to $C_6$ alkyl and $C_1$ to $C_6$ substituted alkyl;

each R$^7$ is independently selected from the group consisting of H, $C_1$ to $C_6$ alkyl, $C_1$ to $C_6$ substituted alkyl, and CF$_3$; and each R$^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

wherein the ratio of ethylene glycol:isatin is about 2 to about 10 mL ethylene glycol:about 1 g isatin and ratio of aqueous hydrazine:isatin is about 1.5: about 3; and (b) isolating said oxindole.

2. The process according to claim 1, wherein said isatin is 7-fluoroisatin.

3. The process according to claim 1, wherein the ratio of ethylene glycol:isatin is about 2 mL ethylene glycol:about 1 g isatin.

4. The process according to claim 1, wherein the ratio of aqueous hydrazine:isatin in step (b) is about 2: about 1.

5. The process according to claim 1, wherein step (a) is performed at about 110 to about 140° C.

6. The process according to claim 5, wherein step (a) is performed at about 120° C.

7. The process according to claim 1, wherein step (a) is performed over about 4 to about 8 hours.

8. The process according to claim 1, wherein an impurity of the following structure is formed in step (a):

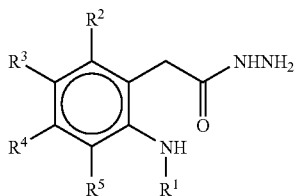

wherein:
- $R^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;
- $R^2$, $R^3$, $R^4$, and $R^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or
- $R^2$ and $R^3$; $R^3$ and $R^4$; $R^4$ and $R^5$; or $R^5$ and $R^1$ are fused to form:
    (i) a 3 to 9 membered carbon-based saturated or unsaturated ring; or
    (ii) a 3 to 9 membered heterocyclic ring containing in its backbone one to three heteroatoms selected from the group consisting of O, S and N;
    wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;
- $R^6$ is selected from the group consisting of $C_1$ to $C_6$ alkyl and $C_1$ to $C_6$ substituted alkyl;
- each $R^7$ is independently selected from the group consisting of H, $C_1$ to $C_6$ alkyl, $C_1$ to $C_6$ substituted alkyl, and $CF_3$; and
- each $R^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy.

9. The process according to claim 8, wherein said impurity is converted to said oxindole using an inorganic acid.

10. The process according to claim 1, wherein said oxindole is converted to an alkylated oxindole, comprising reacting said oxindole with an alkyl halide in the presence of a copper halide or a copper halide adduct.

11. The process according to claim 10, wherein said alkylated oxindole is of the structure:

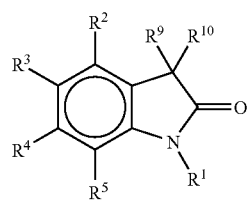

wherein:
- $R^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;
- $R^2$, $R^3$, $R^4$, and $R^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or
- $R^2$ and $R^3$; $R^3$ and $R^4$; $R^4$ and $R^5$; or $R^5$ and $R^1$ are fused to form:
    (i) a 3 to 9 membered carbon-based saturated or unsaturated ring; or
    (ii) a 3 to 9 membered heterocyclic ring containing in its backbone one to three heteroatoms selected from the group consisting of O, S and N;
    wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;
- $R^6$ is selected from the group consisting of $C_1$ to $C_6$ alkyl and $C_1$ to $C_6$ substituted alkyl;
- each $R^7$ is independently selected from the group consisting of H, $C_1$ to $C_6$ alkyl, $C_1$ to $C_6$ substituted alkyl, and $CF_3$;
- each $R^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;
- $R^9$ is $C_1$ to $C_6$ alkyl or $C_1$ to $C_6$ substituted alkyl; and
- $R^{10}$ is H, $C_1$ to $C_6$ alkyl, $C_1$ to $C_6$ substituted alkyl, or $CF_3$.

12. The process according to claim 10, wherein the copper halide adduct is $CuBr \cdot (CH_3)_2S$.

13. The process according to claim 10, which is performed in the presence of a base.

14. The process according to claim 13, where said base is potassium or sodium tert-butoxide.

15. The process according to claim 13, which comprises about 3 to about 6 equivalents of said base.

16. The process according to claim 15, which comprises about 5 equivalents of said base.

17. The process according to claim 10, which is performed at a temperature of about 0 to about 15° C.

18. The process according to claim 17, which is performed at a temperature of about 6 to about 12° C.

19. The process according to claim 10, wherein said alkyl halide is methyl iodide.

20. The process according to claim 10, wherein said alkylated oxindole is isolated by:
    (i) quenching the alkylation with ammonium chloride;
    (ii) extracting the alkylated oxindole with t-butyl methyl ether;
    (iii) removing the t-butyl methyl ether by distillation; and
    (iv) removing residual water from the product of step (iii) using acetic acid.

21. The process according to claim 10, wherein said alkylated oxindole is brominated.

22. The process according to claim 21, wherein said brominated oxindole is of the structure:

23

[Structure: oxindole with Br, R², R⁴, R⁵, R⁹, R¹⁰, R¹, O]

23. The process according to claim 21, wherein said brominated oxindole is coupled with an aryl compound.

24. The process according to claim 23, wherein said coupling is performed in the presence of a palladium catalyst.

25. The process according to claim 24, wherein said palladium catalyst is dichloro bis(triphenylphosphine) palladium (II).

26. The process according to claim 24, further comprising reducing the content of palladium and palladium compounds.

27. The process according to claim 26, wherein said reducing step is performed using N-acetyl-L-cysteine.

28. The process according to claim 23, wherein said coupling is performed using [1,3,6,2]dioxazaborcan-2-yl-1-methyl-1H-pyrrole-2-carbonitrile.

29. A process for preparing an oxindole, said process comprising:
(a) combining about 2 mL ethylene glycol:about 1 g of an isatin of the structure:

[Structure: isatin with R², R³, R⁴, R⁵, R¹]

wherein:
R¹ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

R², R³, R⁴, and R⁵ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or R² and R³; R³ and R⁴; R⁴ and R⁵; or R⁵ and R¹ are fused to form:
(i) a 3 to 9 membered carbon-based saturated or unsaturated ring; or
(ii) a 3 to 9 membered heterocyclic ring containing in its backbone one to three heteroatoms selected from the group consisting of O, S and N;
wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;

24

R⁶ is selected from the group consisting of $C_1$ to $C_6$ alkyl and $C_1$ to $C_6$ substituted alkyl;
each R⁷ is independently selected from the group consisting of H, $C_1$ to $C_6$ alkyl, $C_1$ to $C_6$ substituted alkyl, and $CF_3$; and
each R⁸ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

(b) reacting the solution of step (a) with about 2 equivalents of aqueous hydrazine; and
(c) isolating said oxindole of the structure:

[Structure: oxindole with R², R³, R⁴, R⁵, R¹]

30. A process for preparing an aryl substituted oxindole, said process comprising:
(a) combining about 2 mL ethylene glycol:about 1 g of an isatin of the structure:

[Structure: isatin with R², R³, R⁴, R⁵, R¹]

wherein:
R¹ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

R², R³, R⁴, and R⁵ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or R² and R³; R³ and R⁴; R⁴ and R⁵; or R⁵ and R¹ are fused to form:
(i) a 3 to 9 membered carbon-based saturated or unsaturated ring; or
(ii) a 3 to 9 membered heterocyclic ring containing in its backbone one to three heteroatoms selected from the group consisting of O, S and N;
wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;

R⁶ is selected from the group consisting of $C_1$ to $C_6$ alkyl and $C_1$ to $C_6$ substituted alkyl;
each R⁷ is independently selected from the group consisting of H, $C_1$ to $C_6$ alkyl, $C_1$ to $C_6$ substituted alkyl, and $CF_3$; and each R⁸ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

(b) reacting the solution of step (a) with about 2 equivalents of aqueous hydrazine to form an oxindole of the structure:

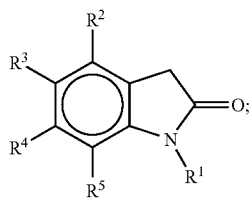

(c) alkylating said oxindole with an alkyl halide in the presence of a copper halide or a copper halide adduct to form an alkylated oxindole of the structure:

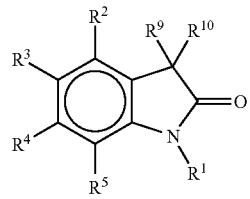

wherein
$R^9$ is $C_1$ to $C_6$ alkyl or $C_1$ to $C_6$ substituted alkyl; and
$R^{10}$ is H, $C_1$ to $C_6$ alkyl, $C_1$ to $C_6$ substituted alkyl, or $CF_3$;

(d) brominating said alkylated oxindole;
(e) coupling said brominated oxindole with an aryl compound in the presence of a palladium catalyst; and
(f) reducing the content of palladium or palladium compounds in the product of step (e) using N-acetyl-L-cysteine.

31. A process for preparing an oxindole of the structure:

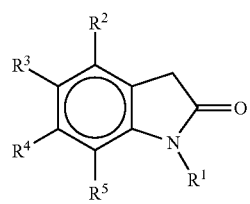

wherein:
$R^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;
$R^2$, $R^3$, $R^4$, and $R^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or $R^2$ and $R^3$; $R^3$ and $R^4$; $R^4$ and $R^5$; or $R^5$ and $R^1$ are fused to form:
(i) a 3 to 9 membered carbon-based saturated or unsaturated ring; or
(ii) a 3 to 9 membered heterocyclic ring containing in its backbone one to three heteroatoms selected from the group consisting of O, S and N;
wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;
$R^6$ is selected from the group consisting of $C_1$ to $C_6$ alkyl and $C_1$ to $C_6$ substituted alkyl;
each $R^7$ is independently selected from the group consisting of H, $C_1$ to $C_6$ alkyl, $C_1$ to $C_6$ substituted alkyl, and $CF_3$; and
each $R^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;
or a pharmaceutically acceptable salt or tautomer thereof;
said process comprising reacting an inorganic acid and a compound of the following structure:

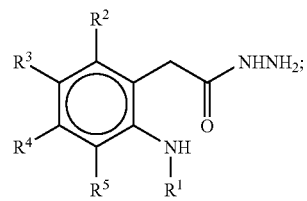

or a pharmaceutically acceptable salt or tautomer thereof.

32. A compound of the structure:

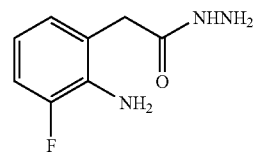

or a pharmaceutically acceptable salt or tautomer thereof.

33. A process for preparing 7-fluoro-2-oxindole, comprising reacting the compound of claim 32 with an inorganic acid.

34. A process for producing an oxindole of the structure:

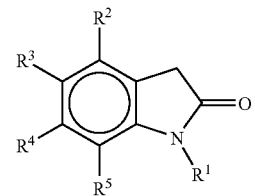

wherein
$R^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

$R^2$, $R^3$, $R^4$, and $R^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or $R^2$ and $R^3$; $R^3$ and $R^4$; $R^4$ and $R^5$; or $R^5$ and $R^1$ are fused to form:
  (i) a 3 to 9 membered carbon-based saturated or unsaturated ring; or
  (ii) a 3 to 9 membered heterocyclic ring containing in its backbone one to three heteroatoms selected from the group consisting of O, S and N;
  wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;

$R^6$ is selected from the group consisting of $C_1$ to $C_6$ alkyl and $C_1$ to $C_6$ substituted alkyl;

each $R^7$ is independently selected from the group consisting of H, $C_1$ to $C_6$ alkyl, $C_1$ to $C_6$ substituted alkyl, and $CF_3$; and each $R^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

said process comprising:
  (a) reacting aqueous hydrazine and an isatin in ethylene glycol, wherein said isatin is of the following structure:

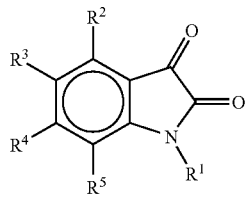

wherein:
  $R^1$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocycle, substituted heterocycle, heteroaryl, and substituted heteroaryl;

$R^2$, $R^3$, $R^4$, and $R^5$ are independently selected from the group consisting of H, halogen, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heterocycle, substituted heterocycle, heteroaryl, substituted heteroaryl, $OR^6$, $N(R^7)_2$, $CON(R^7)_2$, $SO_2N(R^7)_2$, and COOH; or $R^2$ and $R^3$; $R^3$ and $R^4$; $R^4$ and $R^5$; or $R^5$ and $R^1$ are fused to form:
    (i) a 3 to 9 membered carbon-based saturated or unsaturated ring; or
    (ii) a 3 to 9 membered heterocyclic ring containing in its backbone one to three heteroatoms selected from the group consisting of O, S and N;
    wherein rings (i)-(ii) are optionally substituted by 1 to 3 groups selected from the group consisting of $C_1$ to $C_6$ alkyl, substituted $C_1$ to $C_6$ alkyl, halogen, $C_1$ to $C_6$ alkoxy, substituted $C_1$ to $C_6$ alkoxy, and $N(R^8)_2$;

$R^6$ is selected from the group consisting of $C_1$ to $C_6$ alkyl and $C_1$ to $C_6$ substituted alkyl;

each $R^7$ is independently selected from the group consisting of H, $C_1$ to $C_6$ alkyl, $C_1$ to $C_6$ substituted alkyl, and $CF_3$; and each $R^8$ is independently selected from the group consisting of $C_1$ to $C_6$ alkyl, $C_1$ to $C_6$ substituted alkyl, $C_1$ to $C_6$ alkoxy, and substituted $C_1$ to $C_6$ alkoxy;

wherein the ratio of ethylene glycol:isatin is about 2 to about 10 mL ethylene glycol:about 1 g isatin and the ratio of aqueous hydrazine:isatin is about 1.5: about 3;
(b) cooling the product of step (a) to about room temperature;
(c) adding water to the product of step (b);
(d) adding an inorganic acid to the product of step (c);
(e) cooling the product of step (d); and
(f) collecting the product of step (e) using filtration.

* * * * *